United States Patent [19]

Rausis

[11] Patent Number: 5,074,862

[45] Date of Patent: Dec. 24, 1991

[54] SURGICAL EQUIPMENT

[76] Inventor: Claude F. Rausis, Diolly, 1950 Sion, Switzerland

[21] Appl. No.: 362,969

[22] Filed: Jun. 8, 1989

[30] Foreign Application Priority Data

Jun. 16, 1988 [CH] Switzerland ............ 2331/88

[51] Int. Cl.$^5$ ............................................. A61N 5/06
[52] U.S. Cl. ......................................... 606/19; 606/10; 606/14; 128/6; 128/395; 604/20; 604/22; 604/27
[58] Field of Search ........................... 128/4–6, 128/395, 397, 398, 898, 897; 606/10-19; 219/121.67, 121.84; 604/20, 22, 27

[56] References Cited

U.S. PATENT DOCUMENTS

| | | | |
|---|---|---|---|
| 3,818,913 | 6/1974 | Wallach | 604/22 |
| 4,185,633 | 1/1980 | Prozorov et al. | 606/17 |
| 4,489,712 | 12/1984 | Ohshima | 128/6 |
| 4,641,635 | 2/1987 | Yabe | 128/6 |
| 4,676,242 | 6/1987 | Doi | 128/398 |

FOREIGN PATENT DOCUMENTS

| | | | |
|---|---|---|---|
| 0194856 | 9/1986 | European Pat. Off. | |
| 0258901 | 3/1988 | European Pat. Off. | |
| 2740969 | 3/1979 | Fed. Rep. of Germany | 128/398 |
| 3730494 | 3/1988 | Fed. Rep. of Germany | 128/395 |
| 61-103690 | 5/1986 | Japan | |
| 1142125 | 2/1985 | U.S.S.R. | 128/395 |
| 1266540 | 10/1986 | U.S.S.R. | 128/395 |
| 1289461 | 2/1987 | U.S.S.R. | 128/395 |
| 1316675 | 6/1987 | U.S.S.R. | 128/395 |

Primary Examiner—Stephen C. Pellegrino
Assistant Examiner—David Shay
Attorney, Agent, or Firm—Young & Thompson

[57] ABSTRACT

The surgical equipment comprises a sealed $CO^2$ working laser (13) and a sighting He Ne-laser (12) the beams of which are superimposed; a cooling circuit of the working laser comprising a heat exchanger the secondary of which is fed with a liquid circulated by a pump (24), the same pump feeding through the intermediary of a three-way valve (25), either the said secondary circuit of the heat exchanger, or a duct feeding a nozzle emitting a water jet. The beams of the lasers and the duct feeding the nozzle are housed in a supple or articulated arm (10) connected to the hand piece (11) into which is further inserted thermographic visualization equipment of the operating field.

6 Claims, 1 Drawing Sheet

SURGICAL EQUIPMENT

The present invention has for its object the provision of surgical equipment permitting a surgeon to cut off, to resect, to trim, to take out and to treat human or animal living tissues by using so-called non-tactile surgery, that is to say without direct contact between a cutting instrument such as a scalpel, scissors or the like, and the tissue structures of the patient.

Non-tactile surgery has been used since the introduction of the laser beam in the medical field and more precisely the $CO_2$-laser. In fact, the $CO_2$ gas laser, the most appropriate for surgical purposes, enables working at a distance without touching the tissues. It has proven its clinical experimental efficiency with respect to the use of a conventional scalpel:

surgery without effusive bleeding due to its hemostatic effect on small vessels, so that vision of the surgeon will not be obstructed, absence of traumatic tissue manipulation because the $CO_2$-laser emanates from a distance with no metallic or other contact in the operating field, better sterilization due to working from a distance and to the immediate destruction of material at the impact point, including germs, reduction of pain during the healing process.

Despite unquestionable successes, the $CO_2$-laser has not yet reached a complete degree of trustworthiness. It still has a few weak spots and evident gaps.

However, the laser as well as the scalpel remains superficial in its action, at the more or less enlarged focalisation point of the beam. This $CO_2$-laser does not cope with the bleeding of big vascular branches as they are encountered in the important vital organs of the organism.

The second example of non touching surgery is now realized by the advent of new surgical equipment which emits a fine or coarse water jet at more or less high pressure (cf. "Resection of the liver with a water jet", Br. J. Surg. Vol 69 (1982) 93–94 printed in Great Britain).

This chirurgical technique by a distant action with a pressurized water jet is particularly worthwhile for the preparation-resection of parenchy neutral tissues having a lower resistance to the water jet than the sustaining conjunctive structures such as the big vascular branches.

These two techniques of non-tactile surgery thus become complementary, so that the first aim of the present invention is to provide non-tactile surgical apparatus combining the two effects: $CO_2$-laser and water jet at high pressure, in only one hand piece for the surgeon and which further permits a pharmacologic treatment of the operating field as well as a simultaneous thermographic visualization of the effect of the laser as well as of the water jet on the treated tissues.

The attached drawing shows schematically and by way of example one embodiment of the surgical equipment according to the invention.

Figure 1:
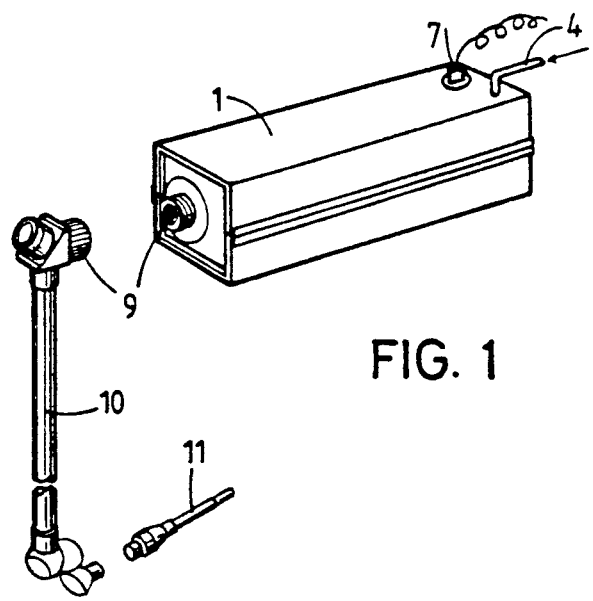
FIG. 1 is a general perspective view of it.

FIG. 1 shows very schematically the surgical equipment according to the invention which comprises a casing 1 housing the visualization laser 12, the working laser 13, the water jet creating device as well as the electronic and thermographic equipment. This casing 1 the different elements of which will be described in more detail hereinafter, is provided on the one hand with connections 2 permitting connecting it to an electrical current source of 220 volts feeding the two lasers 12, 13, to a source of pressurized fluid 4, generally air; to a water feed 5; to an additive duct 6; to a current source 7, and to a TV output 8. On the other hand this casing is provided with a multiple connector 9 enabling to connecting it to an articulated arm or flexible cable 10 the end of which is provided with a hand piece 11. This flexible arm or supple cable 10 enables feeding from the casing 1 to the output of the hand piece the visualization and working laser beams, the water jet as well as the linkage of the thermographic gauge to its feeding and data treatment electronic equipment.

Figure 2:
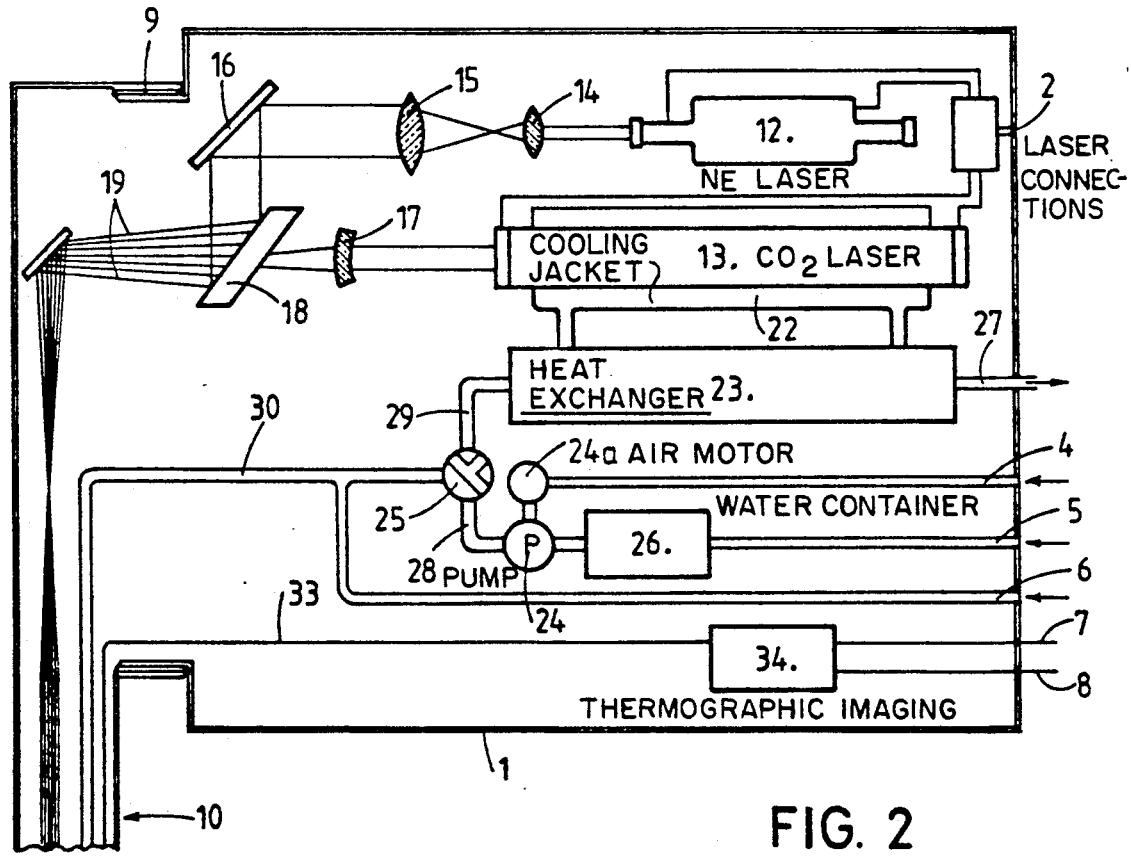
FIG. 2 shows schematically the devices producing the laser beam, the water jet and delivering the thermographic data on the operating field.
Figure 3:
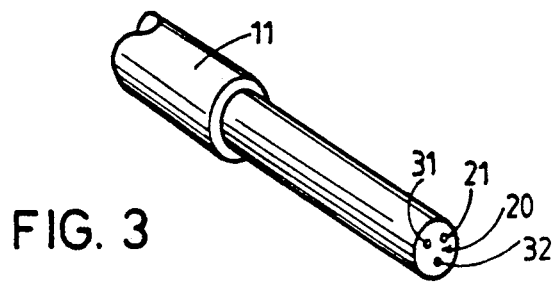
FIG. 3 shows schematically and partially a hand piece according to the invention.

Referring now more particularly to FIG. 2, one sees that the casing houses a first visualization Ne He-laser 12 and a second working $CO_2$-laser 13, whose beams are directed by means of lenses 14, 15 and of a mirror 16 and a lens 17 onto a common mirror 18. So at the output of the casing 1 the visible beam of the laser 12 and the invisible beam of the working laser 13 are strictly combined or superimposed and can be focussed on a same point permitting the operator to see the impact point and the precision of focus of the working laser beam 13 by watching that of the visualization laser 12. This combined beam 19 is fed by mirrors through the articulated arm 10 or through an optical fibre (not shown) through a flexible cable up to the front face 20 of the hand piece 11 whence it emerges through an opening 21.

The two lasers 12 and 13 are of the sealed type, the working $CO_2$-laser 13, which emits substantial energy, having such power that it is necessary to provide for a cooling circuit of this laser. This cooling circuit comprises a jacket 22 surrounding the laser tube 13 connected in closed heat exchange circuit with the primary of a heat exchanger 23, the secondary of which is connected to a circulating pump 24, driven by means of a pressurized air motor 24A, and through the intermediary of a three-way valve 25 to a cooling liquid container 26, fed with liquid by a duct 5, and to an evacuation outlet 27 which can be reconnected in closed circuit for feeding again the container 26. Therefore, when the three-way valve 25 connects the ducts 28 and 29 the heat created by the working laser 13 can be evacuated.

In a variant the $CO_2$-laser can be air cooled, in this case the circuit 22 would be directly connected to the pressurized air circuit 4.

The pump 24 driven by an air motor 24a fed by the pressurized air duct 4 through a three-way valve would feed directly the duct 30 with water.

Thanks to this original conception it has been possible by means of the same pump 24, when the three-way valve is in its other position, connecting the duct 28 to a duct 30, to feed with pressurized water the nozzle 31 located at the end of the hand piece 11, the duct 30 going through the inside of the articulated arm 10 or of the flexible cable replacing it. Therefore by using the same elements, valve 25, water container 26, it is possible either to cool the working laser 13 when it is in use or to create the water jet used as a non-tactile scalpel When the water jet is in use, it is possible to incorporate in said jet adjuvants or additives by the duct 6, which can be any kinds of medicament, permitting having not only a mechanical action of the jet on the tissues but also a pharmacological and therapeutic effect.

The control member controlling the working of the lasers 12, 13, of the pump 24 and of the valve 25 can either be grouped on the hand piece 11 or on a pedal element which the operator can reach. The hand piece 11 is further equipped with a thermographic gauge 32 connected by means of an electrical cable 33 passing through the articulated arm 10 to electronic equipment 34 located in the casing and the output 8 of which can be connected to a TV screen to give a direct thermographic image of the tissues on which the surgeon works.

This is very important since the healthy tissues and the pathological ones, particularly those of a cancereous tumor, have not the same calorific power and can thus be distinguished the ones from the others by their reaction to the heating caused by the impact of the working laser or by the impact of the water jet.

This surgical equipment is unique in that it permits grouping in only one apparatus and in only one hand piece a $CO^2$-laser scalpel, a high pressure water jet pharmacological scalpel and a thermographic sighting equipment of the operating zone.

This equipment is further remarkable in that the cooling circuit of the working laser 13 is combined with the water jet production system, which simplifies the equipment and renders it very flexible, easy to use, and cheaper to manufacture than the separate apparatuses.

The great advantage of this combined surgical equipment is that the surgeon can at any time during the operation work with the laser scalpel or the water jet scalpel and adapt the non-tactile surgical technique as a function of the tissues to be cut or treated. One can further by modulating the pressure of the water jet use it to clean and wash the operating field and feed to it specific pharmacological agents such as anesthesic agents, chemotherapic agents, aseptic agents, hemostatic agents, etc., which constitutes a very useful and important feature in most of the surgical operations performed nowadays.

I claim:

1. A surgical instrument for non-contact surgery, comprising: a working laser means for emitting an operative laser beam; an aiming laser means for emitting a visible laser beam; means for superimposing the working and visible laser beams so that said beams travel a common path; the working laser means including a cooling means for cooling the working laser means by means of a fluid which is circulated by a pressurized air source; a nozzle means for emitting a water jet capable of cutting tissue; a water pump means for supplying water for said jet through a duct to said nozzle means; means for driving said water pump means including said pressurized air source; an articulated arm which incorporates said path and said duct; and a hand piece connected to the articulated arm.

2. A surgical instrument according to claim 1, wherein the cooling means for the working laser means comprises a heat exchanger in a secondary circuit of which a liquid flows which is circulated by said pump means; the said pump means selectively feeding, through a three-way valve, either said secondary circuit of the heat exchanger, or the duct feeding said nozzle means emitting the water jet.

3. A surgical instrument according to claim 1, wherein the source of pressurized air feeds, through a three-way valve, either said cooling means for the working laser, or said means driving the water pump means.

4. A surgical instrument according to claim 1, which comprises further a water tank connected to the pump and from which the water pump draws water.

5. A surgical instrument according to claim 1, wherein said duct of the nozzle means is connected to a duct permitting incorporating in the pumped liquid pharmacologic additives.

6. A surgical instrument according to claim 1, wherein the hand piece is provided with a thermographic gauge for giving a thermographic image of tissue, connected by an electrical linkage passing along the interior of the articulated arm to electronic equipment including output means for delivering signals which generate a thermographic display giving an image of an operating field.

* * * * *